(12) United States Patent
Brahm et al.

(10) Patent No.: US 10,596,203 B1
(45) Date of Patent: Mar. 24, 2020

(54) CUSTOMIZED REPAIR CONSTRUCTS AND METHOD OF PREPARATION

(71) Applicant: Brahm Holdings, LLC, Germantown, TN (US)

(72) Inventors: Timothy R. Brahm, Germantown, TN (US); Jerry Chang, Greenville, SC (US)

(73) Assignee: Brahm Holdings, LLC, Germantown, TN (US)

( * ) Notice: Subject to any disclaimer, the term of this patent is extended or adjusted under 35 U.S.C. 154(b) by 0 days.

(21) Appl. No.: 14/879,543

(22) Filed: Oct. 9, 2015

Related U.S. Application Data

(60) Provisional application No. 62/062,208, filed on Oct. 10, 2014.

(51) Int. Cl.
| | |
|---|---|
| *A61K 35/50* | (2015.01) |
| *A61L 27/38* | (2006.01) |
| *A61F 2/02* | (2006.01) |
| *A61K 35/51* | (2015.01) |

(52) U.S. Cl.
CPC ............ *A61K 35/50* (2013.01); *A61F 2/02* (2013.01); *A61K 35/51* (2013.01); *A61L 27/3834* (2013.01)

(58) Field of Classification Search
CPC ..................................................... A61K 35/50
See application file for complete search history.

(56) References Cited

U.S. PATENT DOCUMENTS

| | | | | |
|---|---|---|---|---|
| 6,986,739 B2 * | 1/2006 | Warren | ............... | A61B 5/0066 118/683 |
| 9,132,156 B1 * | 9/2015 | Werber | ............... | A61K 35/50 |
| 2015/0224226 A1 | 8/2015 | Bhatia et al. | | |
| 2015/0246072 A1 | 9/2015 | Bhatia et al. | | |

FOREIGN PATENT DOCUMENTS

WO    WO 09/052132   *  4/2009  ............... C12N 5/08

OTHER PUBLICATIONS

Murphy et al, "Amniotic Fluid and Placental Membranes: Unexpected Sources of Highly Multipotent Cells", Semin Reprod Med. Jan. 2013, vol. 31, pp. 62-68.*
Barlow et al, "Comparison of Human Placenta- and Bone Marrow-Derived Multipotent Mesenchymal Stem Cells" Stem Cells and Development, 2008, vol. 17, No. 6, pp. 1095-1108.*
Xuan et al, "A specific groove design for individualized healing in a canine partial sternal defect model by a polycaprolactone/hydroxyapatite scaffold coated with bone marrow stromal cells" J Biomed Mater Res A, 2014, vol. 102A, pp. 3401-3408.*
Karacal et al, "Effect of Human Amniotic Fluid on Bone Healing" 2005, Journal of Surgical Research, vol. 129, pp. 283-287. (Year: 2005).*
Werber et al, "A Prospective Study of 20 Foot and Ankle Wounds Treated with Cryopreserved Amniotic Membrane and Fluid Allograft" 2013. The Journal of Foot and Ankle Surgery, vol. 52, pp. 615-621. (Year: 2013).*
Griffey, "Types of 3D Printing: Fused Deposition Modeling", American Library Association, Nov. 5, 2014.http://www.ala.org/tools/article/ala-techsource/types-3d-printing-fused-deposition-modeling (Accessed Sep. 3, 2018) (Year: 2014).*
"Tissue" Merriam-Webster Online Dictionary, 2019. https://www.merriam-webster.com/dictionary/tissue. Retrieved Jan. 22, 2019 (Year : 2019).*
Lee et al, "Solid Free-form Fabrication Technology and Its Application to Bone Tissue Engineering" 2010, vol. 3, No. 2, pp. 85-95. (Year: 2010).*
Prusa et al, "Amniotic fluid cells and human stem cell research—a new connection" Med Sci Monit, 2002, vol. 8, No. 11, pp. RA253-257. (Year: 2002).*
Leong et al, Biomaterials, 2003, vol. 24, pp. 2363-2378. (Year: 2003).*

* cited by examiner

*Primary Examiner* — Allison M Fox
(74) *Attorney, Agent, or Firm* — Barnes & Thornburg LLP

(57) ABSTRACT

Customized, three-dimensionally printed constructs useful for promoting tissue repair and methods of preparing the same are provided.

2 Claims, No Drawings

CUSTOMIZED REPAIR CONSTRUCTS AND METHOD OF PREPARATION

CROSS-REFERENCE TO RELATED APPLICATIONS

The present application claims the benefit of U.S. provisional application No. 62/062,208 filed Oct. 10, 2014, the contents of each are incorporated herein by reference in their entirety.

FIELD OF THE INVENTION

Customized, three-dimensionally printed constructs useful for promoting tissue repair and methods of preparing the same are provided.

BACKGROUND OF THE INVENTION

Human placental tissue has been used in various surgical procedures, including skin transplantation and ocular surface disorders, for over a century. The tissue has been shown to provide good wound protection, prevent surgical adhesions, reduce pain, reduce wound dehydration, and provide anti-inflammatory and anti-microbial effects. The constructs derived from human placental tissue are often difficult to size appropriately for the particular wound or surgical site. Further, a tissue repair site may exhibit an odd shape such that a square, rectangle, or circular shaped (i.e., standard shaped) is not ideal for coverage or incorporation into the tissue repair site. Thus, there exists a need for customized constructs based on the exact measurements of a tissue repair site such that the minimum amount of construct needed for the repair is utilized yet the tissue repair site receives the appropriate level of treatment and improved outcomes.

SUMMARY OF THE INVENTION

According to one aspect, a method for preparing a customized tissue repair construct is provided. The method includes the step of providing a scaffold adapted to support a plurality of tissue cells or a flowable/injectable human birth tissue product. The method further includes the step of infiltrating the scaffold with a plurality of tissue cells or a flowable/injectable human birth tissue product to form a tissue repair construct. The scaffold is prepared according to a predetermined size thereby resulting in a customized tissue repair construct. The predetermined size is based on the size of the tissue repair site. According to one embodiment, the tissue cells are derived from human placental tissue. According to one embodiment, the tissue cells are be combined with one or more bioactive agents including minerals, growth factors, antibiotics, chemotherapeutic agents, antigen, antibodies, enzymes, vectors for gene delivery, and hormones. According to one embodiment, the scaffold is fabricated by an additive manufacturing process. According to one embodiment, the additive manufacturing process is Direct Metal Laser Sintering (DMLS) process, an Electron Beam Melting (EBM) process, Selective Laser Sintering (SLS), Fused Deposition Modeling (FDM), Stereolithography (SLA), Laminated Object Manufacturing, Powder Bed and Inkjet Head 3D Printing, or Plaster-Based 3D Printing (PP). According to one embodiment, the scaffold is fabricated by a bioprinting method. According to one embodiment, the bioprinting method is photolithography, magnetic bioprinting, stereolithography, or direct cell extrusion. According to one embodiment, the scaffold includes at least one biomaterial such as, for example, human placental tissue, human placenta derived extracellular matrix (ECM), collagen, glycosaminoglycans, fibronectin, laminin, and a biologically active gel.

According to another aspect, a method of tissue repair is provided. The method includes the steps of measuring a tissue repair site, providing a scaffold for support of a plurality of tissue cells or a flowable/injectable human birth tissue product, infiltrating the scaffold with a plurality of tissue cells or a flowable/injectable human birth tissue product to form a tissue repair construct, and applying the tissue repair construct to the tissue repair site. The scaffold includes dimensions derived from the tissue repair site size and shape. According to one embodiment, the tissue cells or the flowable/injectable human birth tissue product are derived from human placental tissue. According to one embodiment, the tissue cells are or the flowable/injectable human birth tissue product are combined with one or more bioactive agents selected from the group consisting of minerals, growth factors, antibiotics, chemotherapeutic agents, antigen, antibodies, enzymes, vectors for gene delivery, and hormones. According to one embodiment, the scaffold is fabricated by a three-dimensional bioprinting process. According to one embodiment, the step of measuring the tissue repair site is performed by a three-dimensional scanner. According to one embodiment, the step of measuring the tissue repair site is performed by a computed tomography (CT) scanner. According to one embodiment, the scaffold includes at least one biomaterial such as, for example, human placental tissue, human placenta derived extracellular matrix (ECM), collagen, glycosaminoglycans, fibronectin, laminin, and a biologically active gel.

According to another aspect, a customized tissue repair construct is provided. The construct includes a scaffold adapted to support of a plurality of tissue cells or a flowable/injectable human birth tissue product. The scaffold is sized according to a particular tissue repair site's size and shape. According to one embodiment, the tissue cells are derived from human placental tissue.

According to another aspect, a method for preparing a customized tissue repair construct is provided. The method includes fabricating a scaffold comprising human placental tissue according to a bioprinting method. The scaffold is prepared according to a predetermined size thereby resulting in a customized tissue repair construct.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used herein, "human placental tissue" and "human birth tissue" encompass one or more of the tissue components of the placental organ including, but not limited to, the placental globe, the umbilical cord, the chorionic membrane, the amniotic membrane, and other gelatins, cells and extracellular material.

As used herein, "flowable/injectable human birth tissue product" refers to a composition that is derived from both human placental tissue and amniotic fluid and formulated in a manner that produces a product that is capable of flowing and being injected.

As used herein, "biomaterial" refers to any acceptable naturally-occurring or synthetic matter that safely interacts with living mammalian cells (e.g., biocompatible) and provides the building material for three-dimensional scaffolds as provided herein.

As used herein, "tissue repair site" refers to any site on or within a mammal's anatomy in need of treatment including, but not limited to, wounds, burns, ulcers, or surgical sites (internal or external including sites on or within organs). Exemplary tissue repair sites include diabetic ulcers, decubitus ulcers, venous leg ulcers, arterial leg ulcers, and cutaneous ulcers; surgical sites arising from various procedures including, but not limited to, spine surgeries, knee surgeries, shoulder surgeries, OB/GYN procedures, urological procedures, plastic surgeries, trauma-related cases, cardiovascular procedures, brain/neurological procedures, sport injury surgeries; soft tissue repair; burn and wound care; or a tissue repair site arising from any procedure where a wound covering or an anti-adhesion barrier is desirable.

Provided herein are tissue repair constructs that aid in the healing cascade, reduce pain, reduce wound dehydration, provide anti-inflammatory and anti-microbial effects, and prevent adhesion formation. The tissue repair constructs are sized or dimensioned on a customized basis such that each construct is tailored in size and shape to fit a particular tissue repair site. By customizing the construct, the tissue repair site receives a construct that is better fitted thereby improving outcomes and minimizing construct tissue waste.

According to one embodiment, the tissue repair construct as provided is fabricated from cells, tissue, or a combination thereof that are bioprinted to a three dimensional scaffold. The resulting construct may be fabricated in a manner that results in construct capable of bearing a load.

According to one embodiment, the three dimensional scaffold is a synthetic scaffold, a scaffold prepared from biomaterials, or a combination thereof. According to one embodiment, the scaffold is prepared from polycaprolactone (PCL). According to another embodiment, the scaffold is prepared from a variety of biomaterials such as, for example, human placenta derived extracellular matrix (ECM), collagen, glycosaminoglycans, fibronectin, laminin or a combination thereof. According to another embodiment, the scaffold is prepared from a combination of PCL and ECM. According to another embodiment, the scaffold is prepared from a biologically active gel. The gel may include, for example, alginate, hyaluronic acid, growth factor β1, antibiotics, gelatin, or a combination thereof.

According to another embodiment, the scaffold is prepared entirely from human placental tissue. According to such an embodiment, the scaffold does not require seeding with additional tissue cells after the scaffold is fabricated.

The scaffolds as provided herein may be fabricated using additive manufacturing processes known in the art that typically involve making objects from three-dimensional model data by joining materials together in a layer-by-layer fashion. Suitable additive manufacturing processes include, but are not limited to, Direct Metal Laser Sintering (DMLS) process, an Electron Beam Melting (EBM) process, Selective Laser Sintering (SLS), Fused Deposition Modeling (FDM), Stereolithography (SLA), Laminated Object Manufacturing, Powder Bed and Inkjet Head 3D Printing (e.g., binder jetting), Plaster-Based 3D Printing (PP), a directed energy deposition process, or any combination thereof.

According to a preferred embodiment, the scaffolds as provided herein are fabricated according to an acceptable three-dimensional printing technique suitable for biomaterials (e.g., bioprinting). According to one embodiment, a computer is used to control the printing process and to form three-dimensional structures. According to one embodiment, suitable fabrication techniques include, but are not limited to, photolithography, magnetic bioprinting, stereolithography, and direct cell extrusion. According to a preferred embodiment, the scaffolds as provided herein may be fabricated with a bioprinter (e.g., 3D-Bioplotter® available from EnvisionTEC of Dearborn, Mich.). According to one embodiment, the bioprinter is used for deposition of multiple synthetic or biological materials using pressure. According to such an embodiment, the bioprinter includes multiple syringes with needles that move in three dimensions (x, y, z) to extrude multiple materials at the same time to fabricate the scaffold. Air or mechanical pressure is applied to the syringe which then deposits a strand of material for the length of movement and time the pressure is applied. Parallel strands are plotted in one layer. For the following layer, the direction of the strands is turned over the center of the object, creating a fine mesh with good mechanical properties and mathematically well-defined porosity. The bioprinting of the scaffold is preferably carried out in sterile environments (e.g., in a laminar flowbox). According to one embodiment, ECM is applied to the sides of a bioprinted PCL scaffold and subject to a dehydration process. According to another embodiment, PCL and ECM are both printed into a layered scaffold. According to one embodiment, the scaffold is bioprinted entirely from human placental tissue.

The scaffolds as provided herein may be sized and shaped according to a predetermined set of measurements. According to one embodiment, the scaffold size is programmed into the computer controlling the bioprinter's scaffold fabrication. According to one embodiment, the size of the scaffold is determined by measuring a tissue repair site in need of treatment. According to one embodiment, the scaffold size is approximately the same size as the targeted tissue repair site. According to yet another embodiment, the scaffold size is slightly larger than the target tissue repair site to allow for the application of sutures, glue, or other affixing means. Alternatively, the scaffold size is adjusted to accommodate the increased size from seed cell or tissue growth. According to one embodiment, the thickness of the scaffold may vary depending on the type of tissue repair site and the number of successive layers within the scaffold. Thus, the scaffold thickness may be fabricated in any anatomically acceptable size.

The tissue repair site may be measured by various procedures that result in an accurate representation of the site. According to one embodiment, a medical professional physically measures the site and manually programs the sizes into the computer responsible for scaffold fabrication. According to another embodiment, a three-dimensional image of the tissue repair site is acquired using panoramic, high resolution scanning equipment to produce an image from which exact measurements of the tissue repair site may be extrapolated. According to one embodiment, a three-dimensional scanner is used to gather the dimensional data. According to one embodiment, the high resolution scanning is carried out by a computed tomography (CT) scanner. According to one embodiment, a computer aided design (CAD) package is utilized to interpret the data for subsequent fabrication of the scaffold.

After fabrication, the scaffold as provided herein may be seeded with tissue cells or a flowable/injectable human birth tissue product. According to a preferred embodiment, the scaffold is seeded with tissue cells or a flowable/injectable human birth tissue product capable of aiding in the healing cascade at the tissue repair site. According to one embodiment, a bioreactor is utilized to allow the tissue cells or flowable/injectable human birth tissue product to infiltrate and encompass the scaffold. According to a preferred embodiment, after infiltration, the scaffold absorbs back into itself, leaving behind a fully cellular tissue repair construct to use in or on a tissue repair site. According to a preferred embodiment, the tissue cells or the flowable/injectable human birth tissue product are derived from human placental tissue.

Human placental tissue as utilized in the tissue repair constructs as provided herein are preferably recovered from a full-term Cesarean delivery of a newborn. Alternatively, human placental tissue is recovered from a full-term vaginal delivery of a newborn. The subsequent steps of preparing the human placental tissue material are performed in a controlled environment (i.e., certified biological safety cabinet, hood or clean room). Instruments, solutions, and supplies coming into contact with the human birth tissue material during processing are sterile. All surfaces coming in contact with the human placental tissue material intended for transplant are either sterile or draped using aseptic technique. Infectious disease testing of donor blood specimens is performed for each tissue donor on a specimen collected at the time of donation or within seven days prior to or after donation. Advantageously, the methods that are used to screen for a communicable disease follow the regulations as set forth by the Federal Drug Administration and the American Association of Tissue Banks. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

According to one embodiment, the tissue cells or the flowable/injectable human birth tissue product may be combined with one or more additional drugs. According to one embodiment, the one or more additional drugs are loaded in the construct and adapted for controlled or extended release. According to one embodiment, the tissue cells or the flowable/injectable human birth tissue product may be combined with one or more additional bioactive agents such as physiologically compatible minerals, growth factors, antibiotics, chemotherapeutic agents, antigen, antibodies, enzymes, vectors for gene delivery and hormones.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention claimed is:

1. A method for preparing a customized tissue repair construct for a specific tissue repair site comprising
    measuring the tissue repair site via a three-dimensional scanner or computed tomography (CT) scanner;
    preparing a scaffold according to an additive manufacturing process selected from the group consisting of direct metal laser sintering (DMLS) process, an electron beam melting (EBM) process, selective laser sintering (SLS), stereolithography (SLA), and laminated object manufacturing; and
    infiltrating the scaffold with a flowable/injectable human birth tissue product consisting of amniotic fluid and human amniotic membrane to form a tissue repair construct,
    wherein the scaffold consists of one or more biomaterials selected from the group consisting of human placenta derived extracellular matrix (ECM), glycosaminoglycans, fibronectin, and laminin, and
    wherein the scaffold is prepared according to a predetermined size based on the size of the tissue repair site thereby resulting in a customized tissue repair construct.

2. A method of tissue repair comprising
    measuring a tissue repair site;
    preparing a scaffold according to a bioprinting process;
    infiltrating the scaffold with a flowable/injectable human birth tissue product consisting of amniotic fluid and human amniotic membrane to form a tissue repair construct; and
    applying the tissue repair construct to the tissue repair site,
    wherein the tissue repair construct aids in healing the tissue repair site,
    wherein the scaffold consists of one or more biomaterials selected from the group consisting of human placenta derived extracellular matrix (ECM), glycosaminoglycans, fibronectin, and laminin, and
    wherein the step of measuring the tissue repair site is performed by a three-dimensional scanner or computed tomography (CT) scanner.

* * * * *